United States Patent [19]

Smith

[11] Patent Number: 5,391,824
[45] Date of Patent: Feb. 21, 1995

[54] STABILIZED LITHIUM REAGENTS

[76] Inventor: W. Novis Smith, 412 S. Perth St., Philadelphia, Pa. 19147

[21] Appl. No.: 747,285

[22] Filed: Aug. 19, 1991

[51] Int. Cl.$^6$ ............... C07C 209/90; C01D 15/00
[52] U.S. Cl. ........................... 564/2; 564/463; 423/179.5
[58] Field of Search ............... 564/2, 463; 423/179.5

[56] References Cited

U.S. PATENT DOCUMENTS

| | | | |
|---|---|---|---|
| 4,595,779 | 6/1986 | Morrison et al. | 564/2 |
| 5,068,368 | 11/1991 | Smith et al. | 568/780 |

OTHER PUBLICATIONS

Lochmann et al., J. Of Organometallic Chemistry, 179(1979), 123–132.
Kamienski et al, Journal of Organic Chemistry, vol. 30, 1965, pp. 3498–3504.
Organo–Metallic Compounds–G. E. Coates London–Methuen & Co. Ltd.–New York–John Wiley & Sons, 1956.

*Primary Examiner*—Shailendra Kumar
*Attorney, Agent, or Firm*—John Lezdey

[57] ABSTRACT

An ether free organolithium reagent composition comprising a solution of a lithium alkylamide having 4 to 20 carbon atoms, and lithium alkoxide present in a amount to increase the solubility of the lithium alkylamide compound and/or to prevent post precipitation thereof.

19 Claims, No Drawings

STABILIZED LITHIUM REAGENTS

FIELD OF THE INVENTION

The present invention relates to a method for stabilizing and enhancing the solubility of branched lithium alkylamides in hydrocarbon solvents. More particularly, there is provided a means for increasing the solubility of lithium alkylamides in hydrocarbon solvents for use as reagents, and a means for stabilizing the solution containing the desired reagent against post precipitation through the use of lithium alkoxides.

BACKGROUND OF THE INVENTION

It is known that alkali metal organoamides such as lithium diisopropylamide are insoluble of themselves in purely hydrocarbon solvents at ordinary temperatures. Lithium diisopropyl amide has a solubility of 0.2N in heptane (C. W. Kamienski et al, J. Org. Chem. Vol. 30 p. 3498, 1965). It is further known that these hydrocarbon-insoluble alkali metal organoamides can be made soluble in ether-free hydrocarbon solutions by the addition of magnesium bis-diisopropylamide or soluble lithium amides. However, the presence of other organoamides is not always desirable, especially in the case where the particular lithium amide is a reactant and other lithium amides would similarly react and form undesirable side products.

Lithium amides are widely used as reagents in the preparation of pharmaceuticals and specialty chemicals. Lithium amides are particularly useful for the preparation of lithium acetylide compounds which are used to form acetylenic substituted organic compounds such as steroid fragrance intermediates. In order to form the lithium acetylide, acetylene is reacted with a lithium amide such as lithium diisopropyl amide just prior to reacting the newly formed lithium acetylide with the ketone or other reagent in the same reactor. All of these steps are performed below 0° C. Usually, it is necessary to add an ether cosolvent such as tetrahydrofuran at this point to increase the limited solubility of the reagents and the subsequently formed lithium salt of the product from the reaction with the ketone. The lithium amide may be added as a preformed solution or it may be formed in the same reactor by reacting an alkyllithium such as n-butyllithium with an amine such as diisopropylamine. In either case, the lithium amide usually exhibits lower solubility than desired for maximum reactivity and yet there is a need to minimize the amount of solvents employed.

In order to increase the concentration of the lithium amide in the preformed solutions of the prior art, ethers such as tetrahydrofuran and/or complexing agents such as organomagnesium compounds have been added to increase the solubility of the lithium amide in solution. The presence of the ethers makes these solutions unstable and they decompose on standing in storage. The presence of magnesium compounds in the reaction and subsequent workup is undesirable because the possibility of lower reactivity and yields of desired products plus the more difficult workup due to the presence of the formed magnesium oxide which is highly insoluble and formed during washing.

Additionally, when tetrahydrofuran is used as the solvent it has been found necessary to limit the amount of tetrahydrofuran to no more than one mole for each mole of lithium amide in order to minimize degradation of the system.

U.S. Pat. No. 4,595,779 to Morrison et al relates to a composition and method for preparing lithium diisopropyl amide by the reaction of lithium metal and diisopropylamine in tetrahydrofuran and an inert liquid hydrocarbon cosolvent including styrene as an electron carrier. The use of tetrahydrofuran is considered essential in the preparation when utilizing lithium metal.

The article of Keith Smith entitled "Lithiation and Organic Synthesis", *Chemistry In Britain,* January 1982, pages 29–32, discloses the preparation of lithium dialkyl amides for use as lithiating agents by the reaction of organolithium reagents in aliphatic hydrocarbon solvents.

It is an object of the present invention to provide a lithium amide reagent compositions having greater amounts of the lithium amide in solution and not precipitate on standing.

It is a further object of the invention to provide a process for preparing stable lithium amides in higher concentrations in solution and in a hydrocarbon solvent which is stable and free of ethers.

It is understood that the lithium alkoxides used in the invention include the lithium sec-alkoxides and lithium tert-alkoxides having 4 to 20 carbon atoms. These lithium branched alkoxides include lithium isopropoxide, lithium isobutoxide, lithium sec-butoxide, lithium sec-pentoxide, lithium t-butoxide, lithium t-pentoxide, and the like.

SUMMARY OF THE INVENTION

The present invention provides an organolithium composition comprising a solution of a lithium alkylamide having 4 to 20 carbon atoms in the alkyl group in a hydrocarbon solvent and a lithium alkoxide having 4 to 20 carbon atoms, said lithium alkoxide being present in an amount to increase the solubility of the lithium alkylamide and to prevent post precipitation thereof.

Preferably, the solvent is an aliphatic, monocyclic aliphatic or monocyclic aromatic solvent and is ether free.

The presence of about 1 to 50 mole percent of the lithium alkoxide based on the lithium amide in the solvent has been found suitable for increasing the solubility of the lithium amide. The improved solubility is advantageous in large scale operations since the reduction in volume in solvent permits a more efficient process without contending with large solvent recovery. The reagents are particularly advantageous in reactions involving the lithium amides where the lithium alkoxides are non-reactive.

To provide a stabilizing effect on the lithium alkylamide, all that is required is the presence of about 0.02 to 1.0M of the lithium alkoxide in the solution.

The present invention further provides a process for increasing the solubility of a lithium amide, particularly a lithium branched alkylamide in an ether free hydrocarbon solvent by incorporating in the solvent a lithium alkoxide. The lithium alkoxide can be added to the prepared lithium alkylamide solution, incorporated in the solution to be stabilized or prepared simultaneously therewith.

DESCRIPTION OF THE PREFERRED EMBODIMENTS

In accordance with one embodiment of the invention the solubility of a lithium alkylamide having 4 to 20 carbon atoms in the alkyl group is improved in hydrocarbon solvents by providing a lithium alkoxide in the solvent. The additional lithium alkoxide can initially be present, added at any time or can be prepared simultaneously with the lithium alkylamide.

A preferred feature of this embodiment is the preparation of lithium alkylamides or a reagent composition which behaves and reacts similarly to the lithium alkylamides. It has been found that lithium alkylamides will form very concentrated solutions with lithium alkoxides in aliphatic and aromatic solvents. Solutions having concentrations of from 2.0 to 4.0 molar combined lithium alkylamide plus lithium alkoxide can be prepared. The lithium alkoxides help solubilize the lithium alkylamides.

In accordance with another embodiment of the invention, there is prepared a reagent composition comprising an inert hydrocarbon solvent, a lithium amide selected from the group consisting of:

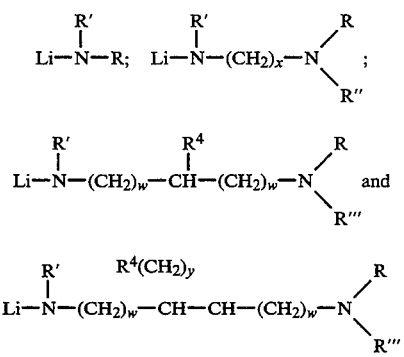

wherein R is a hydrogen, an alkyl of 1 to 8 carbon atoms, alkyl phenyl or an alkyl monocyclic aliphatic group, R' and R" are the same or different and each represent hydrogen, an alkyl of 1 to 8 carbon atoms, alkyl phenyl or an alkyl monocyclic aliphatic group, R''' is hydrogen, alkyl or alkoxy, $R^4$ is hydrogen, alkyl or phenyl, wherein at least one R, R', R" and R''' is hydrogen, W is from 0 to 4, x is an integer of 2 to 8, and y is an integer of 2 to 6, and a solubilizing agent which is a lithium alkoxide having 4 to 20 carbon atoms. The lithium alkoxide is preferably branched.

The solvent which may be used in connection with the present invention alone or in admixture include hydrocarbons such as cycloalkanes, more particularly cyclopentane, cyclohexane, cycloheptane, and the like, aliphatic hydrocarbons such as heptane, hexane, and the like, benzene, toluene, ethyl benzene, cumene, xylene, and the like.

Ethers may be utilized, such as tetrahydrofuran, but the invention provides the advantage that ethers need not be utilized. The amines which may be utilized in the preparation of the lithium amides of the invention include the alkyl amines such as methyl amine, isopropyl amine, isoamyl amine and the like, dialkyl amines such as dimethyl amine, diethyl amine, diisopropyl amine, diisobutyl amine, diisoamyl amine, dialkylpentyl amine, di(alkylhexyl) amine, for example, N,N-di(tert-butyl)ethylene diamine, dimethylaminoethyl amine, dimethylaminopropyl amine, N,N,N-trimethylethylene diamine, N,N-dipropylaminoproylene amine, N,N-diethyl-1,3-propane diamine, N,N-dimethyl-N'-ethylethylene diamine, and the like.

The preferred amines which may be utilized in the invention include n-butyl amine, diisoamyl amine, diisobutyl amine, di-sec butylamine, diisopropyl amine, dimethylaminopropyl amine (DMAPA) and diethylamino ethyl amine.

It should be understood that the presence of the lithium alkoxides is also effective in compositions which contain ethers such as tetrahydrofuran. For example, a solution of lithium diisopropyl amide in 70% heptane—30% tetrahydrofuran can be stabilized with 5 mole percent lithium n-butoxide so that there is no signs of precipitate even after three months at room temperature.

The following table illustrates the solubiltiy of various lithium amides in toluene, cyclohexane and heptane:

TABLE 1

| Starting Amine | Mole % | Solvent | Molar Conc |
|---|---|---|---|
| Diisopropyl amine | 100 | heptane | 0.3 |
| Diisopropyl amine | 100 | toluene | 0.49 |
| Diisobutyl amine | 100 | heptane | 1.08 |
| Diisobutyl amine | 100 | toluene | 2.1 |
| Diisobutyl amine | 100 | cyclohexne | >1.3 |
| Diethyl amine | 100 | heptane | 0.04 |
| Diethyl amine | 100 | toluene | 0.05 |
| Di-sec-butyl amine | 100 | heptane | >1.3 |
| Di-sec-butyl amine | 100 | cyclohexane | >1.3 |
| Dimethylaminopropyl amine (DMAPA) | 100 | cyclohexane | 0.79 |
| Cyclohexyl amine | 100 | toluene | 0.3 |

The following examples are illustrative of the practice of the method of the present invention. It will be understood, however, that is not to be construed as in any way limitative of the full scope of the invention since various changes can be made, without departing from the spirit of the teachings contained herein, in the light of the guiding principles which have been set forth above. All percentages herein stated are based on weight except wherein noted.

EXAMPLE I

Preparation of lithium diisopropylamide/diisobutylamide solution (1:1 mole ratio).

1759 g (7.65 moles) of 24.2% n-butyllithium in cyclohexane is added over a 90-minute period to 3.70 diisopropylamide and 3.70 moles diisobutyl amine containing 0.3 moles tert butyl alcohol in a 5-liter three-necked flask under nitrogen. The mixture was stirred at a temperature of 20°-30° C. Butane gas evolved during the reaction through an oil by bubbler. The reaction was complete upon final addition of the butyllithium solution. The solution was polish filtered. The final product was 2.7M lithium molar mixed lithium diisopropylamide and diisobutylamide with 3% lithium tert butoxide.

EXAMPLE II

Preparation of lithium diisobutylamide.

1686.4 g (6.0M) of 22.8% n-butyllithium in toluene was added over a 90 minute period to 5.85 moles of diisobutylamine containing 0.24 moles n-butanol in a 5 liter three-necked flask under nitrogen. The mixture was stirred at 20°-30° C. The reaction was complete after the final addition of n-butyllithium. The resulting solution contained 2.6M lithium diisobutylamide and was stable to precipitation for over two months.

EXAMPLE III

Preparation of lithium hexamethyleneimide solution.

A. A 2.4M solution of lithium hexamethyleneimide was prepared by adding 24% n-butyllithium in cyclohexane to a stoichiometric amount of hexamethyleneimine under nitrogen. The resulting solution was permitted to sit overnight at room temperature. A yellow precipitate formed. The concentration of the solution was 1.6M lithium hexamethyleneimide.

B. Following the procedure of part A except that the cyclohexane solution contained 0.125M lithium t-pentoxide resulted in a solution of 2.4M lithium hexamethyleneimide which did not precipitate on standing.

EXAMPLE IV

A. A 2.0 molar solution of lithium diisopropyl amide was prepared by the addition of 24% n-butyllithium in cyclohexane to a stoichiometric amount of diisopropylamine under nitrogen. About 25% by volume of tetrahydrofuran was added. In six weeks at room temperature the solution began to show a measurable amount of precipitate and darkening. In two months the concentration of lithium diisopropyl amide in solution was 1.6 molar.

B. Following the procedure of part A, lithium diisopropyl amide was prepared except that 0.1 molar lithium t-pentoxide was present. No precipitation was observed for two months and only slight darkening of the solution occurred. After eight months the assay showed the solution to be 1.90M and stabilized.

EXAMPLE V

Preparation of stabilized lithium diisobutyl amide.

A. 2.8M solution of lithium diisobutyl amide in heptane was prepared by the addition of 24% n-butyllithium in cyclohexane to a stoichiometric amount of diisobutylamine. The solution was made 0.14M with lithium t-pentoxide. The solution remained clear for at least six months.

What is claimed is:

1. An organolithium reagent composition comprising a solution of a lithium alkylamide having an alkyl group with 4 to 20 carbon atoms in a hydrocarbon solvent selected from the group consisting of aliphatic monocyclic aliphatic and monocylic aromatic and lithium alkoxide having 4 to 20 carbon atoms, said lithium alkoxide being present in a sufficient amount to increase the solubility of said lithium alkylamide and to prevent post precipitation thereof.

2. The reagent composition of claim 1 wherein said solvent is selected from the group consisting of benzene, toluene and xylene.

3. The reagent composition of claim 1 wherein said solvent is selected from the group consisting of cyclopentane, cyclohexane and cycloheptane.

4. The reagent composition of claim 1 wherein said solvent is selected from the group consisting of pentane, hexane and heptane.

5. The reagent composition of claim 1 wherein said lithium alkoxide is branched.

6. The reagent composition of claim 5 wherein said lithium alkoxide is selected from the group consisting of lithium isopropoxide, lithium sec-butoxide and lithium sec-pentoxide.

7. The reagent composition of claim 1 wherein said lithium alkoxide is selected from the group consisting of lithium t-butoxide and lithium t-pentoxide.

8. The reagent composition of claim 1 wherein said lithium reagent composition is free of ethers.

9. The reagent composition of claim 1 comprising 1.5 to 4.0 molar solution of said lithium alkylamide.

10. The reagent composition of claim 1 wherein said lithium amide is selected from the group consisting of

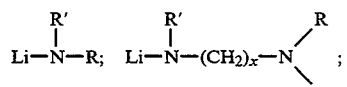

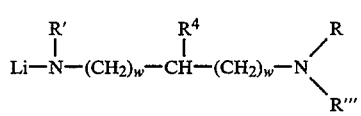

and

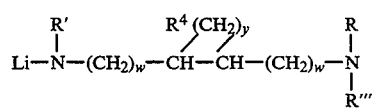

wherein R is a hydrogen, an alkyl of 1 to 8 carbon atoms, alkyl phenyl or an alkyl monocyclic aliphatic group, R' and R" are the same or different and each represent hydrogen, an alkyl of 1 to 8 carbon atoms, an alkyl phenyl, an alkyl monocyclic aliphatic group, R" is hydrogen, alkyl or alkoxy, $R^4$ is hydrogen, alkyl or phenyl, at least one R,R,R" and R'" is hydrogen, W is from 0 to 4, x is an integer of 2 to 8, and y is an integer of 2 to 6.

11. The reagent composition of claim 10 wherein said lithium amide is selected from the group consisting of lithium diisobutylamide and lithium diisopropylamide.

12. The process for increasing the solubility of a lithium alkylamide in a solvent comprising a hydrocarbon solvent selected from the group consisting of aliphatic, monocylic aliphatic and monocyclic aromatic, said process comprising providing said solvent with a lithium alkoxide in an amount sufficient to increase the solubility of said lithium alkylamide and to prevent post precipitation of the lithium alkylamide.

13. The process of claim 12 wherein said lithium alkoxide and lithium alkylamide are prepared simultaneously in situ.

14. The process of claim 12 wherein said lithium alkoxide is lithium t-butoxide.

15. The process of claim 12 wherein said lithium alkoxide is lithium t-pentoxide.

16. The process of claim 12 wherein said solvent is ether free.

17. The process of claim 12 wherein said lithium alkoxide is present in an amount of about 0.02 to 1.0M in the solution.

18. The process of claim 12 wherein said lithium alkoxide is present in an amount of about 1 to 50 mole percent in the solvent.

19. The process of claim 12 wherein said lithium amide is selected from the group consisting of:

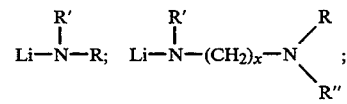

-continued

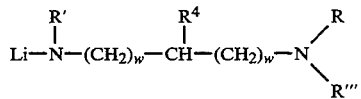

and

-continued

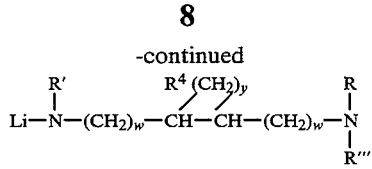

wherein R is a hydrogen, an alkyl of 1 to 8 carbon atoms, alkyl phenyl or an alkyl monocyclic aliphatic group, R' and R" are the same or different and each represent hydrogen, an alkyl of 1 to 8 carbon atoms, an alkyl phenyl, an alkyl monocyclic aliphatic group, R" is hydrogen, alkyl or alkoxy, $R^4$ is hydrogen, alkyl or phenyl, at least one R,R,R" and R'" is hydrogen, W is from 0 to 4,
x is an integer of 2 to 8, and
y is an integer of 2 to 6.

* * * * *